(12) United States Patent
Tsuruta et al.

(10) Patent No.: US 10,479,750 B2
(45) Date of Patent: Nov. 19, 2019

(54) METHOD OF PRODUCING DIALDEHYDE COMPOUND

(71) Applicant: KURARAY CO., LTD., Kurashiki-shi (JP)

(72) Inventors: Takuo Tsuruta, Kamisu (JP); Naoya Minamoto, Tainai (JP); Toshihiro Omatsu, Chiyoda-ku (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 16/081,283

(22) PCT Filed: Feb. 23, 2017

(86) PCT No.: PCT/JP2017/006866
§ 371 (c)(1),
(2) Date: Aug. 30, 2018

(87) PCT Pub. No.: WO2017/150337
PCT Pub. Date: Sep. 8, 2017

(65) Prior Publication Data
US 2019/0023636 A1     Jan. 24, 2019

(30) Foreign Application Priority Data

Mar. 1, 2016 (JP) ................................ 2016-038623

(51) Int. Cl.
*C07C 45/50* (2006.01)
*B01J 31/00* (2006.01)
*C07C 47/12* (2006.01)
*B01J 31/22* (2006.01)

(52) U.S. Cl.
CPC ........... *C07C 45/50* (2013.01); *B01J 31/2221* (2013.01); *C07C 47/12* (2013.01); *B01J 2231/321* (2013.01); *B01J 2531/822* (2013.01); *B01J 2540/525* (2013.01)

(58) Field of Classification Search
CPC .. C07C 45/50; B01J 31/2221; B01J 2231/321
See application file for complete search history.

(56) References Cited

U.S. PATENT DOCUMENTS

| 3,933,920 A | 1/1976 | Nienburg et al. |
| 4,808,756 A | 2/1989 | Tokitoh et al. |
| 5,235,113 A | 8/1993 | Sato et al. |
| 5,312,996 A * | 5/1994 | Packett .................. C07C 45/50 568/451 |
| 5,391,801 A | 2/1995 | Sato et al. |
| 2011/0071321 A1 | 3/2011 | Kreidler et al. |
| 2015/0018576 A1 | 1/2015 | Baumgarten et al. |

FOREIGN PATENT DOCUMENTS

| DE | 2137 603 | 2/1973 |
| EP | 0 088955 | 9/1983 |
| JP | 5-178779 A | 7/1993 |
| JP | 7-281342 A | 10/1995 |
| JP | 11-71318 A | 3/1999 |
| JP | 2009-102244 A | 5/2009 |
| JP | 2011-521990 A | 7/2011 |
| JP | 2015-509491 A | 3/2015 |

OTHER PUBLICATIONS

International Search Report dated May 23, 2017 in PCT/JP2017/006866 filed Feb. 23, 2017.
Longley, R.I. et al., "3,4-Dihydro-2-Methoxy-4-Methyl-2H-Pyran," Organic Syntheses a Publication of Reliable Methods for the Preparation of Organic Compounds, vol. 34, 1954, 3 pages.
Longley, R.I. et al., "3-Methyl-1,5-Pentanediol," Organic Syntheses a Publication of Reliable Methods for the Preparation of Organic Compounds, vol. 34, 1954, 4 pages.
Supplementary European Search Report as received in application EP 17 75 9803.4-1109/3424897 PCT/JP2017006866 dated Sep. 10, 2019.

* cited by examiner

*Primary Examiner* — Sikarl A Witherspoon
(74) *Attorney, Agent, or Firm* — Oblon, McClelland, Maier & Neustadt, L.L.P.

(57) ABSTRACT

A method of producing 1,5-pentanedial having an alkyl group at the 3-position, including a step of hydroformylating an aldehyde compound represented by the following general formula (1):

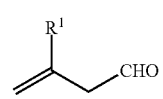

(1)

wherein $R^1$ represents an alkyl group having from 1 to 6 carbon atoms.

13 Claims, No Drawings

METHOD OF PRODUCING DIALDEHYDE COMPOUND

TECHNICAL FIELD

The present invention relates to a method of producing a dialdehyde compound. Specifically, the present invention relates to a method of producing 1,5-pentanedial having an alkyl group at the 3-position.

BACKGROUND ART

Various compounds have been known as 1,5-pentanedial having an alkyl group at the 3-position. For example, 3-methylglutaraldehyde (3-methyl-1,5-pentanedial, which is hereinafter abbreviated as MGL) is a compound that is useful as a curing agent for a photosensitive material, a leather tanning agent, and a synthetic intermediate (see, for example, PTLs 1 to 3). The known production methods of MGL include a method of hydrolyzing pyranyl ether obtained through Diels-Alder reaction of crotonaldehyde and methyl vinyl ether (see NPLs 1 and 2).

CITATION LIST

Patent Literatures

PTL 1: JP 07-281342 A
PTL 2: German Patent No. 2,137,603
PTL 3: JP 2009-102244 A

Non-Patent Literatures

NPL 1: Organic Syntheses, vol. 34, p. 29 (1954)
NPL 2: Organic Syntheses, vol. 34, p. 71 (1954)

SUMMARY OF INVENTION

Technical Problem

The aforementioned ordinary method has room for improvement since the Diels-Alder reaction of crotonaldehyde and methyl vinyl ether has low reactivity and requires severe conditions including a high temperature and a high pressure, the productivity thereof is insufficient due to the prolonged reaction time, and the yield of MGL is low. Accordingly, an object of the present invention is to provide a method of producing 1,5-pentanedial having an alkyl group at the 3-position, such as MGL, under mild conditions with a good yield.

Solution to Problem

The present invention relates to the following items [1] to [4].

[1] A method of producing a dialdehyde compound represented by the following general formula (2) (which is hereinafter referred to as a dialdehyde compound (2)):

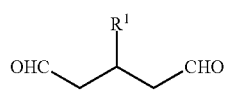

(2)

wherein $R^1$ represents an alkyl group having from 1 to 6 carbon atoms, the method including a step of hydroformylating an aldehyde compound represented by the following general formula (1) (which is hereinafter referred to as an aldehyde compound (1)):

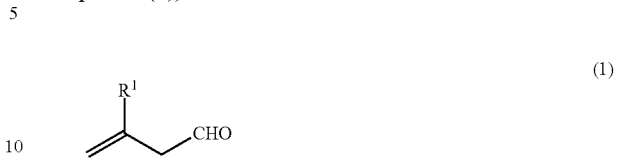

(1)

wherein $R^1$ has the same definition as above.

[2] The production method according to the item [1], wherein the hydroformylating step is performed in the presence of a Groups 8 to 10 metal compound and a ligand.

[3] The production method according to the item [2], wherein the Groups 8 to 10 metal compound is a rhodium compound.

[4] The production method according to the item [2] or [3], wherein the ligand is a compound represented by the following general formula (5):

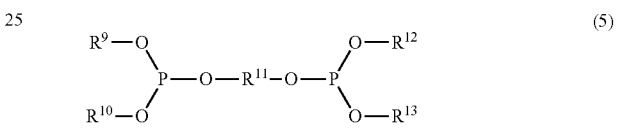

(5)

wherein $R^9$, $R^{10}$, $R^{12}$, and $R^{13}$ each independently represent a hydrocarbon group having from 1 to 40 carbon atoms, which may have a substituent, in which $R^9$ and $R^{10}$, and $R^{12}$ and $R^{13}$ each may be bonded to each other; and $R^{11}$ represents a hydrocarbon crosslinking group having from 1 to 40 carbon atoms, which may have a substituent.

Advantageous Effects of Invention

According to the present invention, 1,5-pentanedial having an alkyl group at the 3-position can be produced under mild conditions with a good yield.

DESCRIPTION OF EMBODIMENTS

In the present invention, the dialdehyde compound (2) is produced through hydroformylation reaction of the aldehyde compound (1).

The aldehyde compound (1) has a double bond at the end thereof, and thus there is a possibility that a part thereof is isomerized to an internal olefin (1)' in the presence of a metal compound. The isomerization of an olefin is generally reversible reaction, but in the case of the isomerization reaction of the aldehyde compound (1), it can be estimated that the reverse reaction unlikely occurs since the internal olefin (1)' produced is a trisubstituted olefin and simultaneously an α,β-unsaturated carbonyl compound, and thus is relatively stable. The hydroformylation reaction of the aldehyde compound (1) has a concern that the yield of the dialdehyde compound (2) is decreased due to the aforementioned isomerization, and therefore it is common sense that a method using the reaction is not considered as a production method of the dialdehyde compound (2). However, as a result of the investigation by the present inventors, it has been surprisingly found that the dialdehyde compound (2) can be produced under milder conditions than the ordinary methods with a good yield by using the reaction.

In the aldehyde compound (1) and the dialdehyde compound (2), the alkyl group having from 1 to 6 carbon atoms represented by $R^1$ may be straight-chain, branched, or cyclic, and examples thereof include a methyl group, an ethyl group, a n-propyl group, an isopropyl group, a n-butyl group, an isobutyl group, a t-butyl group, a n-pentyl group, a n-hexyl group, a cyclopropyl group, a cyclobutyl group, a cyclopentyl group, a methylcyclopentyl group, and a cyclohexyl group. Among these, a methyl group, an ethyl group, and a n-propyl group are preferred, a methyl group and an ethyl group are more preferred, and due to easiness in production of the aldehyde compound (1), and the like, a methyl group is particularly preferred.

The production method of the aldehyde compound (1) is not particularly limited, and the compound may be produced by the known methods. For example, 3-methyl-3-buten-1-al can be synthesized from isoprenol according to the method described in JP2007-525522 A and WO2008/037693.

The dialdehyde compound (2) can be obtained through hydroformylation reaction of the aldehyde compound (1).

The hydroformylation reaction can be performed by reacting the aldehyde compound (1) with carbon monoxide and hydrogen in the presence of a Groups 8 to 10 metal compound and depending on necessity a ligand.

Examples of the Groups 8 to 10 metal compound include a rhodium compound, a cobalt compound, a ruthenium compound, and an iron compound. Examples of the rhodium compound include $Rh(acac)(CO)_2$, $Rh(acac)_3$, $RhCl(CO)(PPh_3)_2$, $RhCl(PPh_3)_3$, $RhBr(CO)(PPh_3)_2$, $Rh_4(CO)_{12}$, and $Rh_6(CO)_{16}$. Examples of the cobalt compound include $HCo(CO)_3$, $HCo(CO)_4$, $Co_2(CO)_8$, and $HCo_3(CO)_9$. Examples of the ruthenium compound include $Ru(CO)_3(PPh_3)_2$, $RuCl_2(PPh_3)_3$, $RuCl_3(PPh_3)_3$, and $Ru_3(CO)_{12}$. Examples of the iron compound include $Fe(CO)_5$, $Fe(CO)_4PPh_3$, and $Fe(CO)_4(PPh_3)_2$. Among these, a rhodium compound is preferably used since relatively mild conditions can be easily selected, and $Rh(acac)(CO)_2$ and $Rh(acac)_3$ are particularly preferably used from the standpoint of the availability.

The amount of the Groups 8 to 10 metal compound used is preferably in a range of from 0.0001 to 100 mmol, and more preferably in a range of from 0.005 to 10 mmol, in terms of metal atom per 1 L of a reaction mixed liquid. When the amount of the Groups 8 to 10 metal compound used is less than 0.0001 mmol in terms of metal atom per 1 L of a reaction mixed liquid, there is a tendency that the reaction rate becomes extremely small, and when the amount thereof exceeds 100 mmol, the effect corresponding to the use amount cannot be obtained, but the catalyst cost is increased.

The ligand used is not particularly limited, and the known ones may be used. Examples of the ligand include compounds represented by the following general formulae (3) to (5), a phosphoramidite (see WO2003/018192, WO2002/083695, WO2004/026803, WO2006/045597, WO2003/066642, WO2000/005641, WO1999/065606, and WO1999/046044), a phosphite having a particular crosslinked structure (see WO1995/000525 and WO2001/058589), a phosphine having a particular substituent (see WO2003/053571, WO2003/053572, WO2009/059963, and WO2000/069801), a phosphabenzene (see WO1997/046507 and WO2000/055164), and a phosphine having a particular crosslinked structure (see WO2001/085661).

Specifically, the compounds described in pages 9 to 40 of JP2007-506691 A may be used.

The ligands may be used alone or as a combination of two or more kinds thereof.

$R^3$ to $R^5$ each independently represent a hydrocarbon group having from 1 to 24 carbon atoms, which may have a substituent, and may be bonded to each other.

$R^6$ to $R^8$ each independently represent a hydrocarbon group having from 1 to 24 carbon atoms, which may have a substituent, and may be bonded to each other.

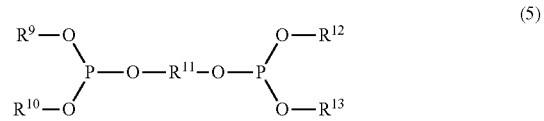

$R^9$, $R^{10}$, $R^{12}$, and $R^{13}$ each independently represent a hydrocarbon group having from 1 to 40 carbon atoms, which may have a substituent, in which $R^9$ and $R^{10}$, and $R^{12}$, and $R^{13}$ each may be bonded to each other; and $R^{11}$ represents a hydrocarbon crosslinking group having from 1 to 40 carbon atoms, which may have a substituent.

In the general formulae (3) and (4), the hydrocarbon group having from 1 to 24 carbon atoms, which may have a substituent, independently represented by each of $R^3$ to $R^8$ may be straight-chain, branched, or cyclic, and examples thereof include an alkyl group, such as a methyl group, an ethyl group, a n-propyl group, an isopropyl group, a n-butyl group, an isobutyl group, a t-butyl group, a n-pentyl group, and a cyclohexyl group; and an aryl group, such as a phenyl group, a naphthyl group, and an anthracenyl group. Among these, a phenyl group and a naphthyl group are preferred.

The hydrocarbon group may have a substituent as far as the hydroformylation reaction is not impaired, and examples of the substituent include an alkyl group, an aryl group, an alkoxy group, a silyl group, an amino group, an acyl group, a carboxy group, an acyloxy group, an amide group, an ionic group, such as $—SO_3M$ (wherein M represents an inorganic or organic cation), a sulfonyl group, a halogen, a nitro group, a cyano group, a fluoroalkyl group, and a hydroxy group.

Examples of the compound represented by the general formula (3) used as the ligand in the present invention include tris(2-methylphenyl) phosphite, tris(2,6-dimethylphenyl) phosphite, tris(2-isopropylphenyl) phosphite, tris(2-phenylphenyl) phosphite, tris(2-t-butylphenyl) phosphite, tris(2-t-butyl-5-methylphenyl) phosphite, tris(2,4-di-t-butylphenyl) phosphite, (2-t-butylphenyl)bis(2-methylphenyl) phosphite, and bis(2-t-butylphenyl)(2-methylphenyl) phosphite, but the compound is not limited thereto. Among these, tris(2-t-butylphenyl) phosphite, tris(2-t-butyl-5-methylphenyl) phosphite, and tris(2,4-di-t-butylphenyl) phosphite are preferred for practicing the present invention industrially.

Specific examples of the compound represented by the general formula (3), in which $R^3$ to $R^5$ are bonded to each other, are shown below, but the compound is not limited thereto.

[Chem. 7]

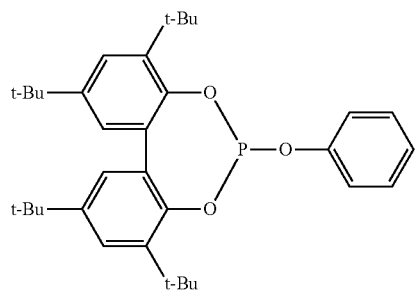

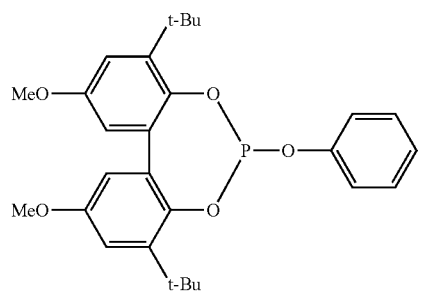

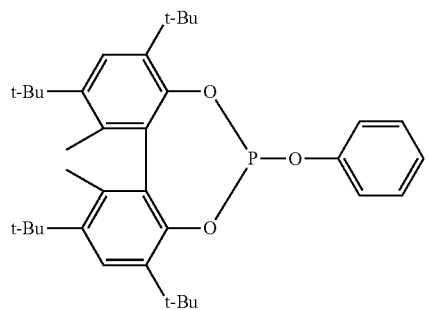

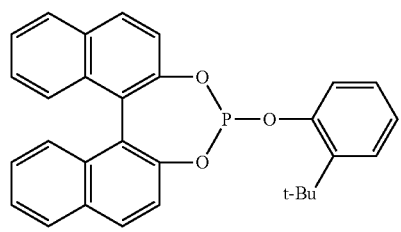

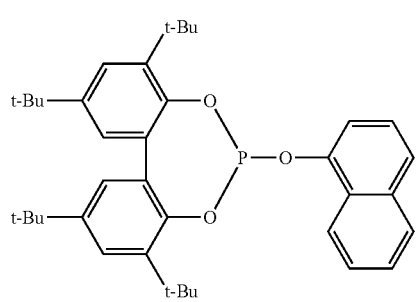

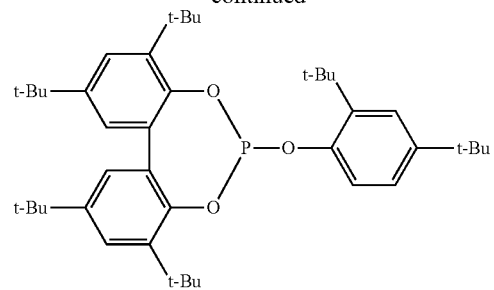

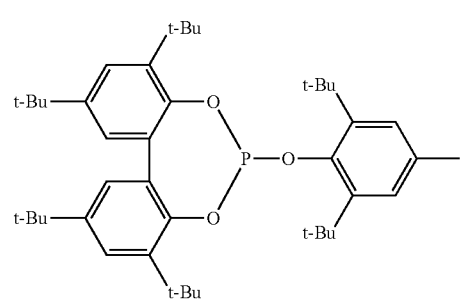

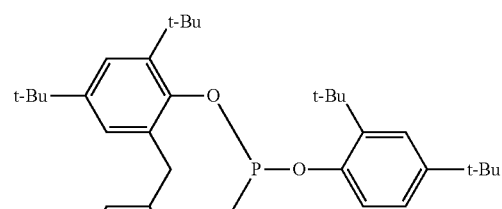

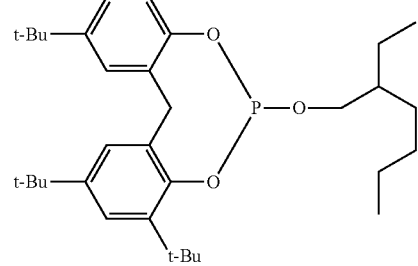

Examples of the compound represented by the general formula (4) used as the ligand in the present invention include an alkali metal salt and an alkaline earth metal salt of triphenylphosphine, tris(4-methylphenyl)phosphine, tris(4-methoxyphenyl)phosphine, tris(4-fluorophenyl)phosphine, tris(4-chlorophenyl)phosphine, tris(dimethylaminophenyl)phosphine, diphenylpropylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine, sulfonated triphenylphosphine, tris(3-sulfophenyl)phosphine, and diphenyl(3-sulfophenyl)phosphine, but the compound is not limited thereto.

In the compound represented by the general formulae (3) and (4), a compound that has an electronic parameter (ν-value) in a range of from 2,065 to 2,090 cm$^{-1}$ and a steric parameter (θ-value) in a range of from 135 to 190° is preferred. These two parameters are values defined according to C. A. Tolman, Chem. Rev., 177, 313 (1977), the electronic parameter is defined by the frequency of the A1 band infrared absorption spectrum of CO of Ni(CO)$_3$L (wherein L represents a ligand) measured in dichloromethane, and the steric parameter is defined by the apex angle of the cone drawn to surround the van der Waals' radius of the outermost atom of the group bonded to the phosphorus atom at the position apart from the phosphorus atom by 2.28 angstrom.

In the general formula (5), the hydrocarbon group having from 1 to 40 carbon atoms, which may have a substituent, independently represented by each of $R^9$, $R^{10}$, $R^{12}$, and $R^{11}$ may be straight-chain, branched, or cyclic, and examples thereof include an alkyl group, such as a methyl group, an ethyl group, a n-propyl group, an isopropyl group, a n-butyl group, an isobutyl group, a t-butyl group, a n-pentyl group, and a cyclohexyl group; and an aryl group, such as a phenyl group, a naphthyl group, and an anthracenyl group. Among these, a phenyl group and a naphthyl group are preferred.

The hydrocarbon group may have a substituent as far as the hydroformylation reaction is not impaired, and examples of the substituent include an alkyl group, an aryl group, an alkoxy group, a silyl group, an amino group, an acyl group, a carboxy group, an acyloxy group, an amide group, an ionic group, such as —SO$_3$M (wherein M represents an inorganic or organic cation), a sulfonyl group, a halogen, a nitro group, a cyano group, a fluoroalkyl group, and a hydroxy group.

Examples of the groups represented by $R^9$ and $R^{10}$, and $R^{12}$, and $R^{13}$, each of which are bonded to each other, and $R^{11}$ include an alkylene group, a cycloalkylene group, a phenylene group, a naphthylene group, and a divalent crosslinking group represented by the following general formula (6).

$$R^{14}{}_m\text{—Ar}^1\text{—(CH}_2)_x\text{-Q}_p\text{-(CH}_2)_y\text{—Ar}^2\text{—R}^{15}{}_n\text{—} \quad (6)$$

$R^{14}$ and $R^{15}$ each independently represent an alkylene group having from 1 to 6 carbon atoms, which may have a substituent; Ar$^1$ and Ar$^2$ each independently represent an arylene group, which may have a substituent; m, n, p, x, y each independently represent 0 or 1; and Q represents a divalent crosslinking group selected from —CR$^{16}$R$^{17}$—, —O—, —S—, —NR$^{18}$—, —SiR$^{19}$R$^{20}$—, and —CO—, wherein R$^{16}$ to R$^{20}$ each independently represent any of hydrogen, an alkyl group having from 1 to 12 carbon atoms, which may have a substituent, a phenyl group, a tolyl group, and an anisyl group.

Examples of the alkylene group include an ethylene group, a trimethylene group, a tetramethylene group, a pentamethylene group, and groups represented by the following formulae.

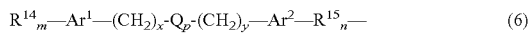

[Chem. 9]

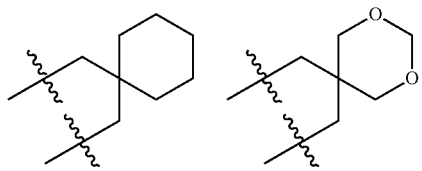

In the formulae, the wavy lines each represent the bonding site.

Examples of the cycloalkylene group include a cyclopropylene group, a 1,2-cyclopentylene group, a 1,3-cyclopentylene group, a 1,2-cyclohexylene group, a 1,3-cyclohexylene group, and a 1,4-cyclohexylene group.

Examples of the phenylene group include a 1,2-phenylene group, a 1,3-phenylene group, and a 1,4-phenylene group.

Examples of the naphthylene group include a 1,2-naphthylene group and a 1,8-naphthylene group.

The groups represented by $R^9$ and $R^{10}$, and $R^{12}$, and RH, each of which are bonded to each other, and $R^{11}$ each may have a substituent, and examples of the substituent include an alkyl group preferably having from 1 to 5 carbon atoms, such as a methyl group, an ethyl group, a propyl group, a butyl group, and a pentyl group; an alkoxy group preferably having from 1 to 4 carbon atoms, such as a methoxy group, an ethoxy group, a propoxy group, and a butoxy group; and an aryl group, such as a phenyl group and a naphthyl group.

In the general formula (6), examples of the alkylene group having from 1 to 6 carbon atoms, which may have a substituent, represented by RH and Rth include an ethylene group, a n-propylene group, a n-butylene group, a n-pentylene group, a n-hexylene group, a 2-methyl-ethylene group, a 1,2-dimethylethylene group, a 2-methyl-n-propylene group, a 2,2-dimethyl-n-propylene group, and 3-methyl-n-pentylene group. Examples of the arylene group represented by Ar$^1$ and Ar$^2$ include a phenylene group, a naphthylene group, and an anthracenylene group. Examples of the alkyl group having from 1 to 12 carbon atoms, which may have a substituent, represented by R$^{16}$ to R$^{20}$ include a methyl group, an ethyl group, a n-propyl group, an isopropyl group, a n-butyl group, an isobutyl group, a t-butyl group, a n-pentyl group, and a cyclohexyl group.

The groups represented by R$^{14}$ to R$^{20}$, Ar$^1$, Ar$^2$ each may have a substituent as far as the hydroformylation reaction is not impaired, and examples of the substituent include an alkyl group, an aryl group, an alkoxy group, a silyl group, an amino group, an acyl group, a carboxy group, an acyloxy group, an amide group, an ionic group, such as —SO$_3$M (wherein M represents an inorganic or organic cation), a sulfonyl group, a halogen, a nitro group, a cyano group, a fluoroalkyl group, and a hydroxy group.

Examples of the compound represented by the general formula (5) are shown below, but the compound is not limited thereto.

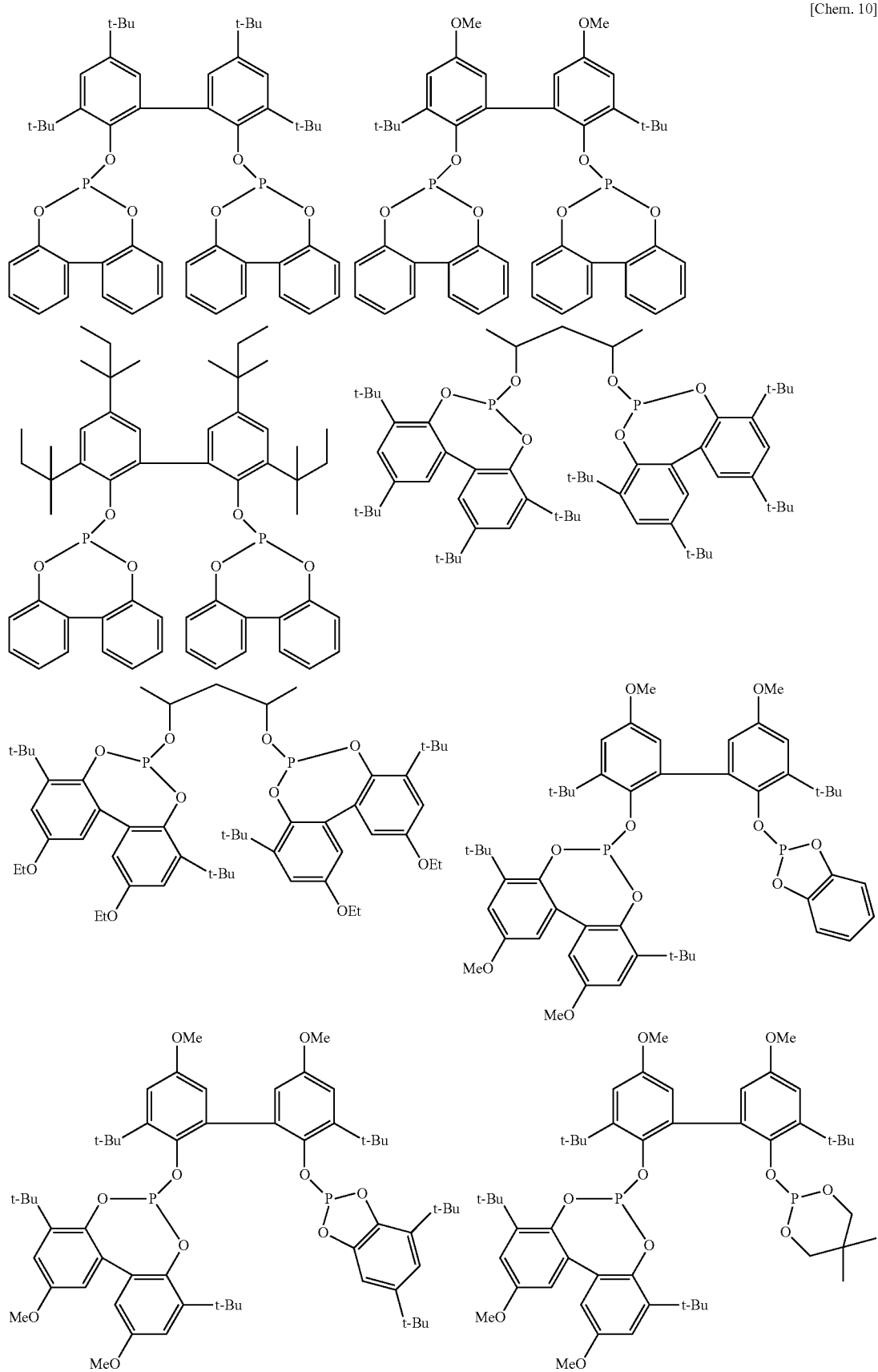

-continued
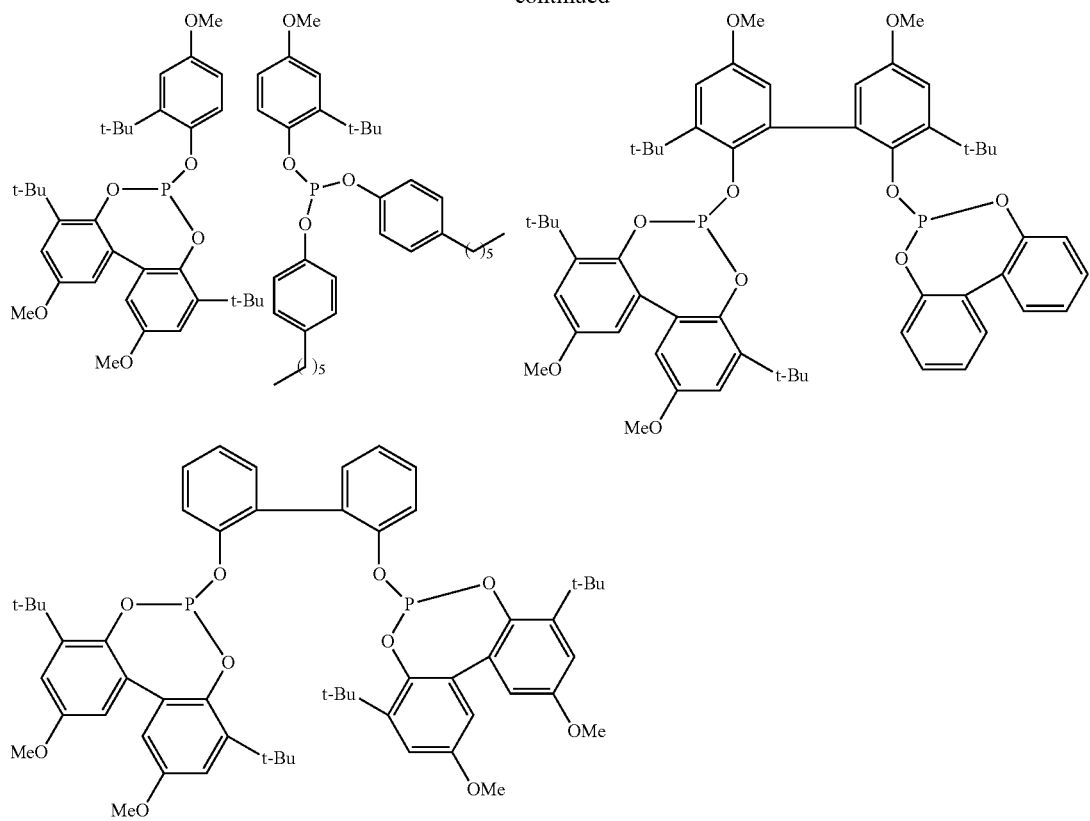
[Chem. 11]
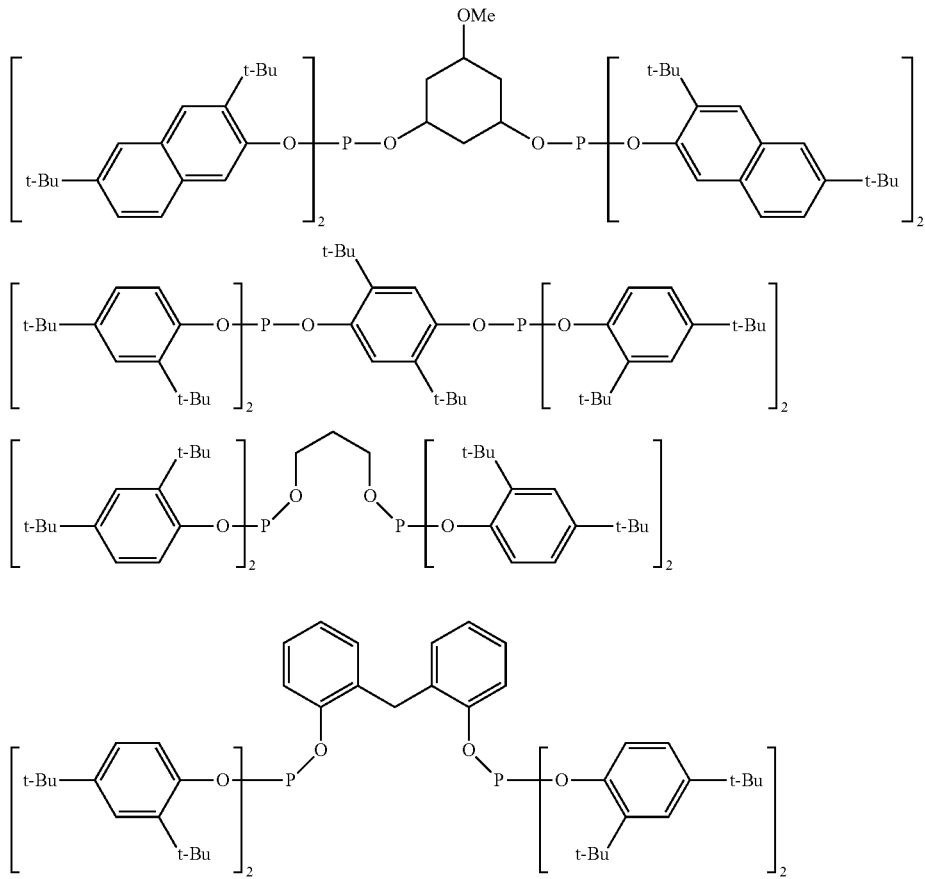

-continued
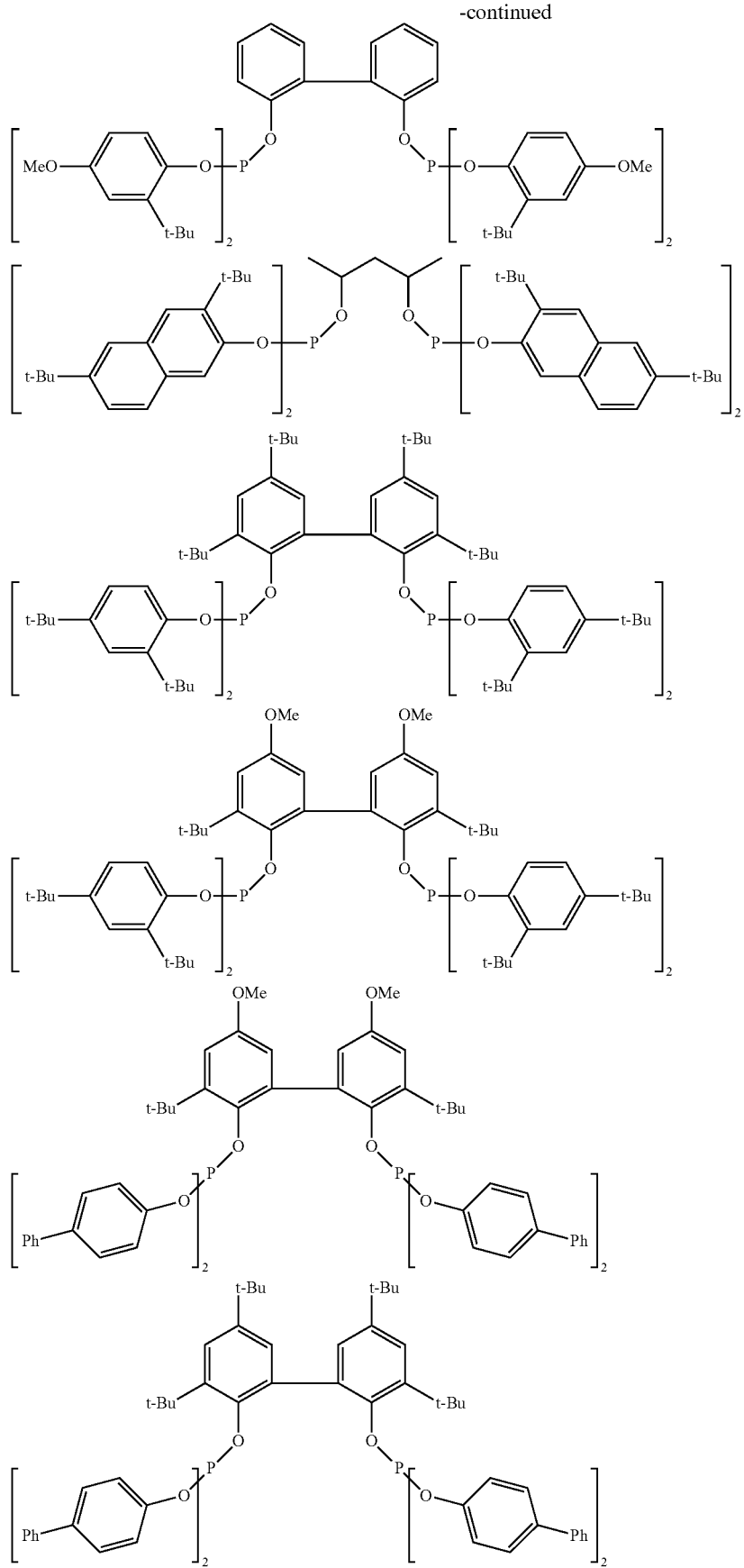

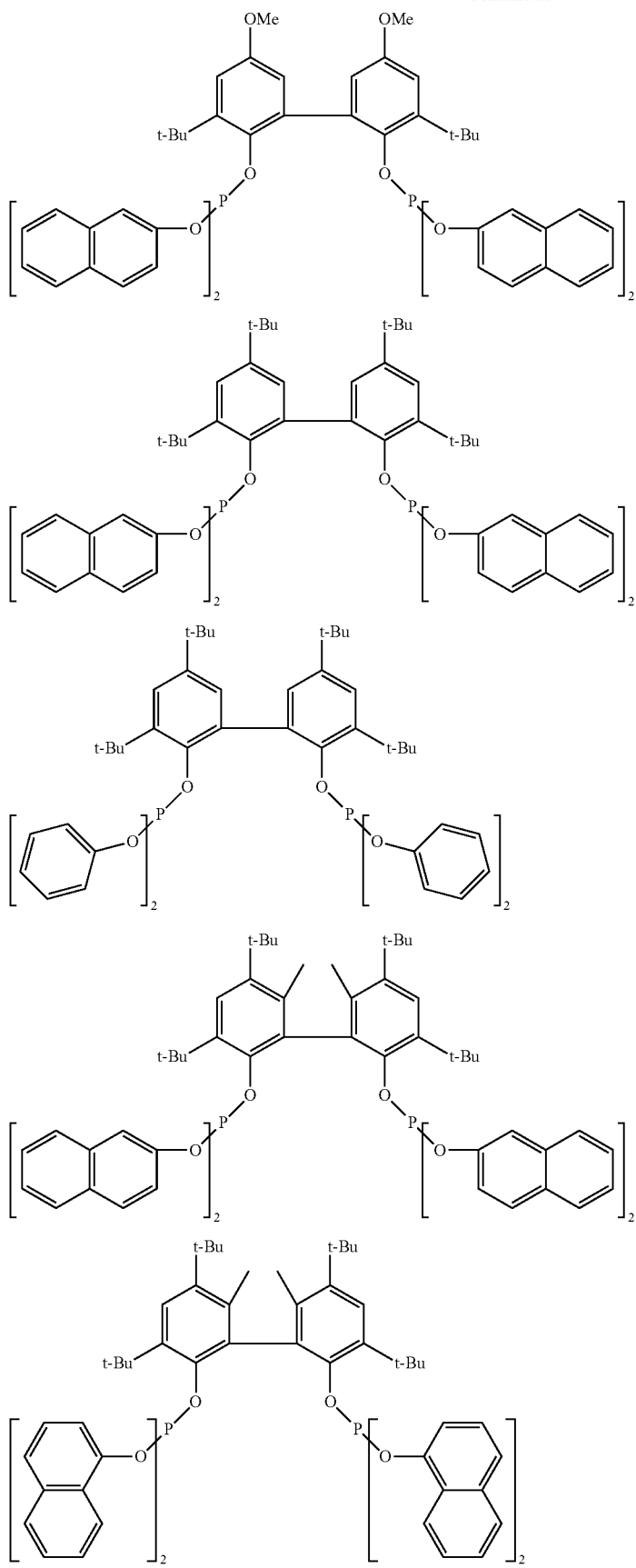

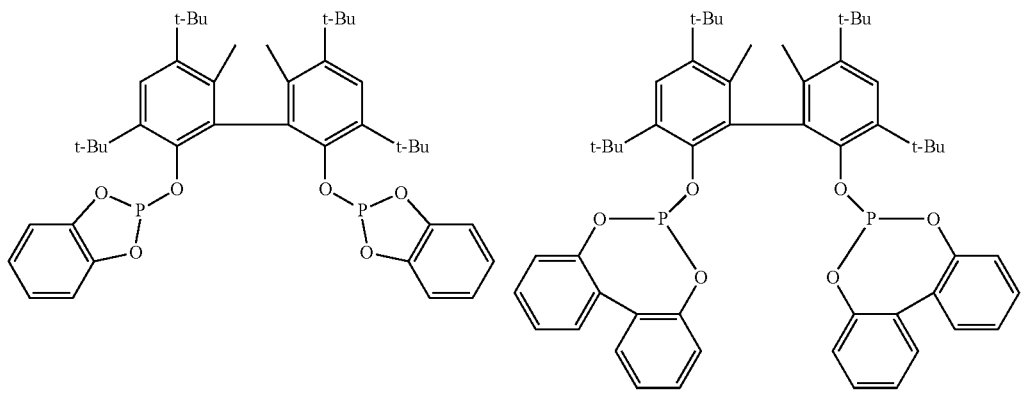
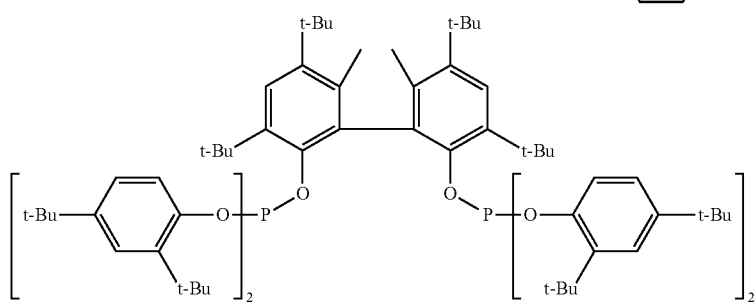
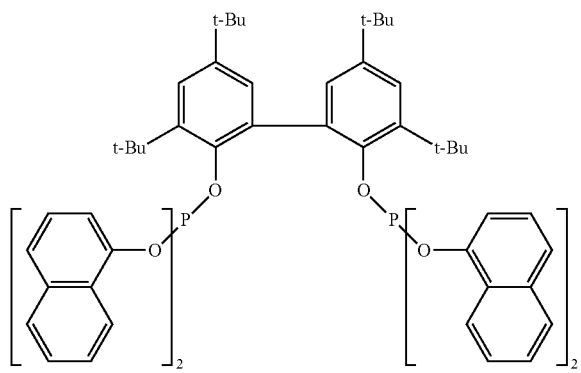
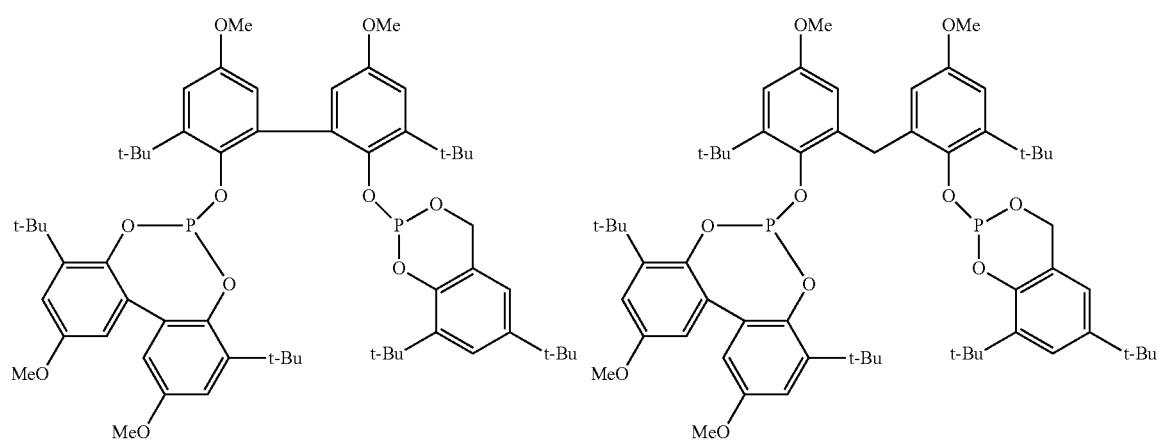

-continued
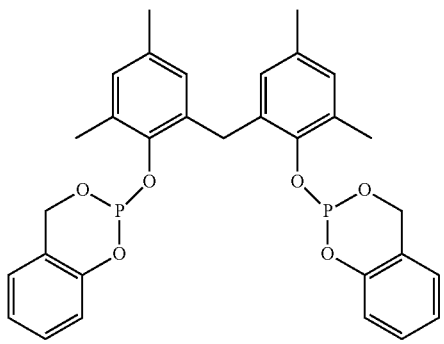
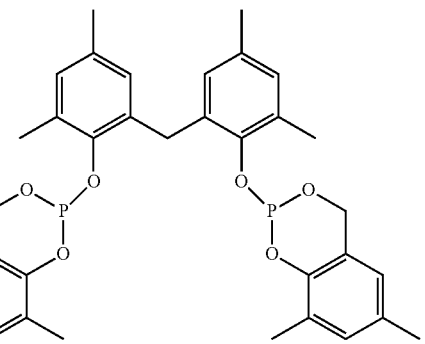
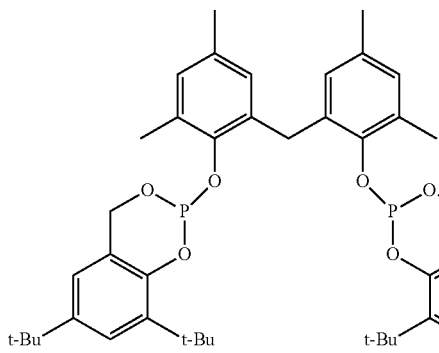
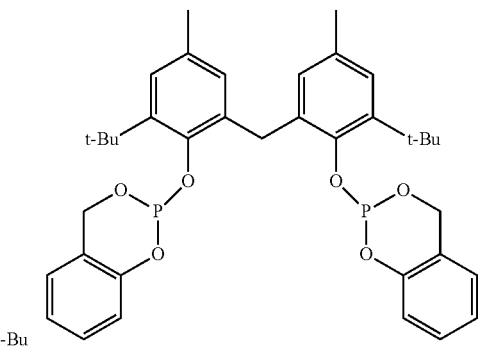
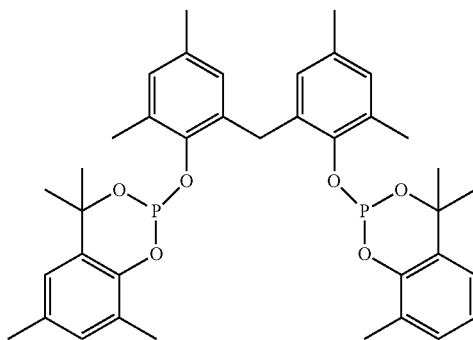
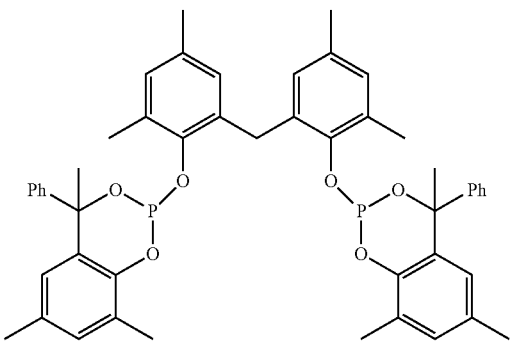
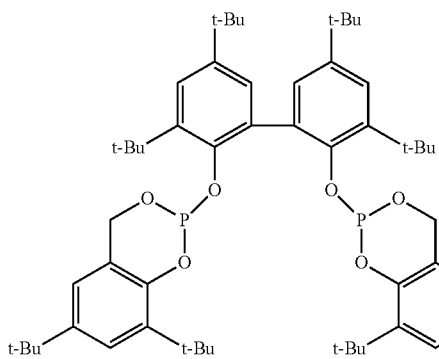
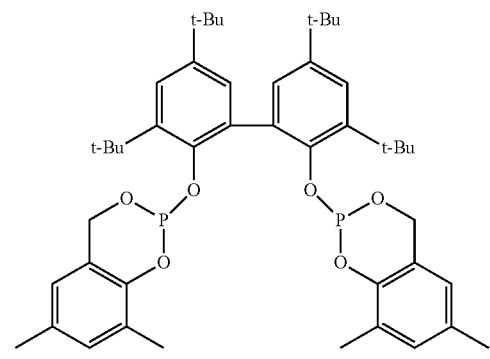
[Chem. 13]

-continued
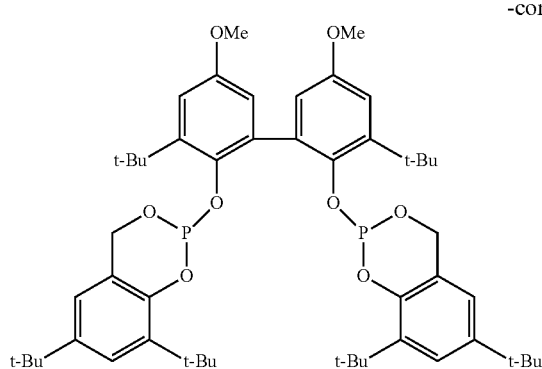
[Chem. 14]
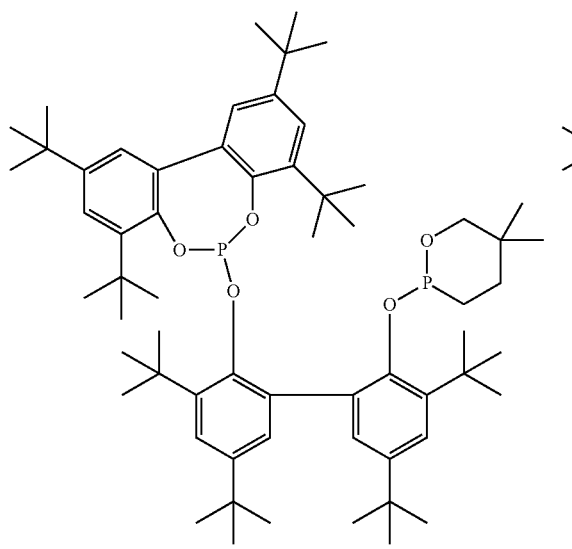
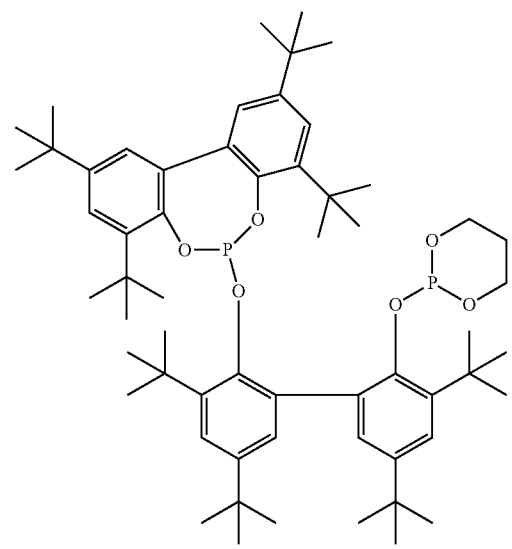
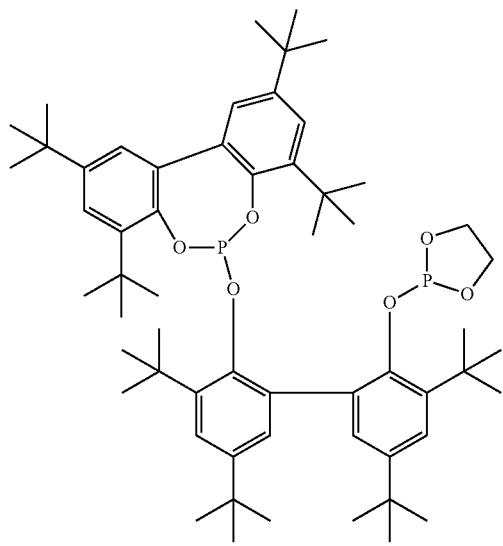
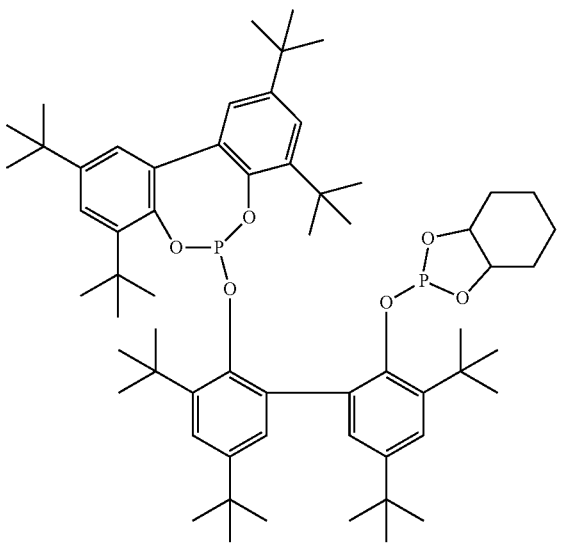

23
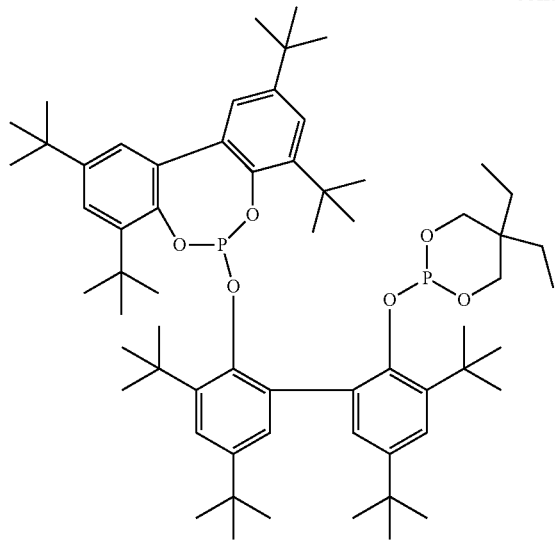
24
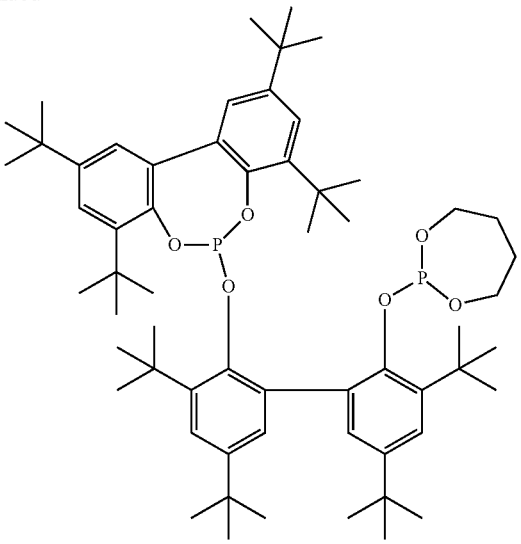
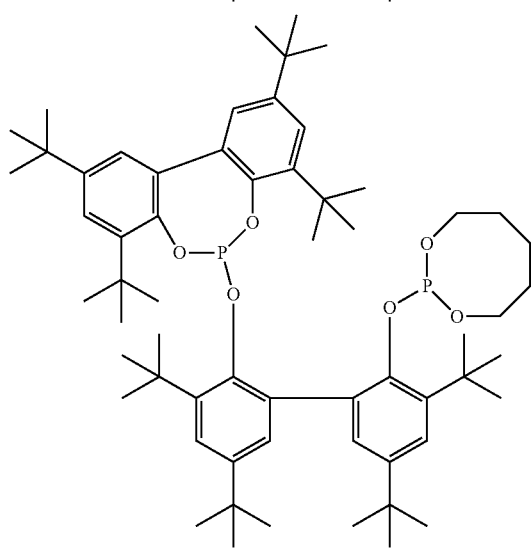
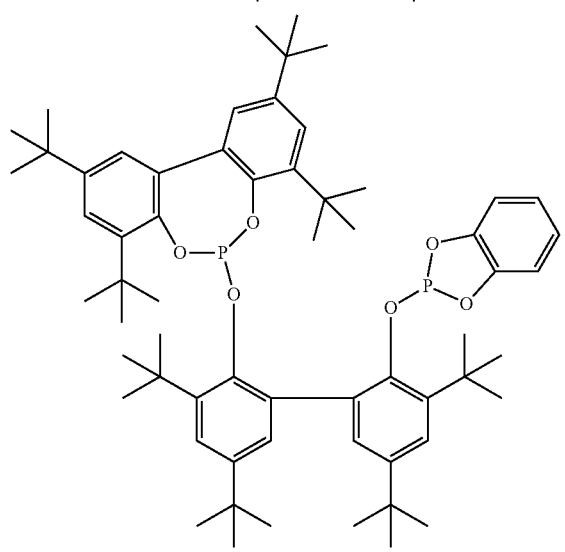
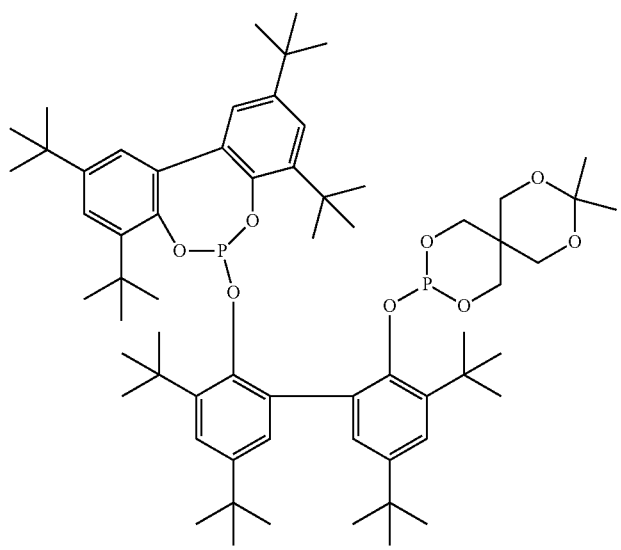

-continued
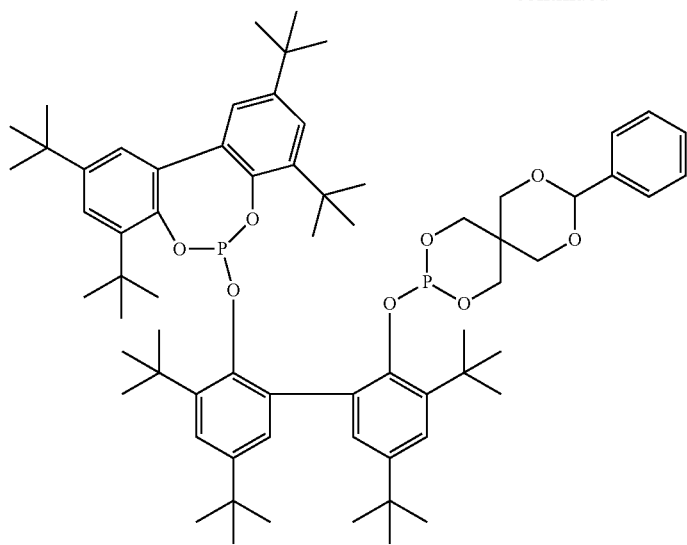
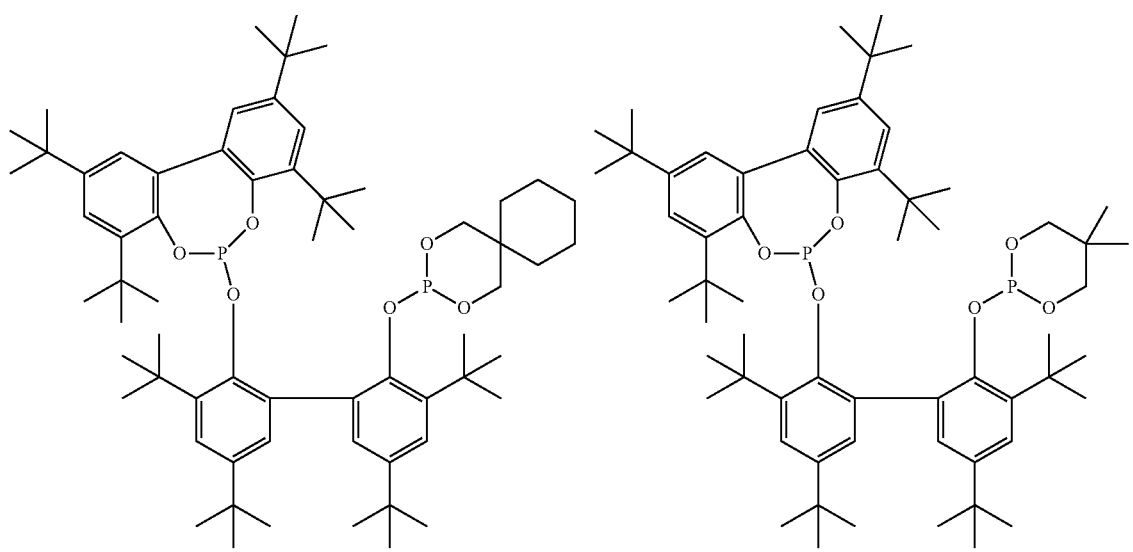
[Chem. 15]
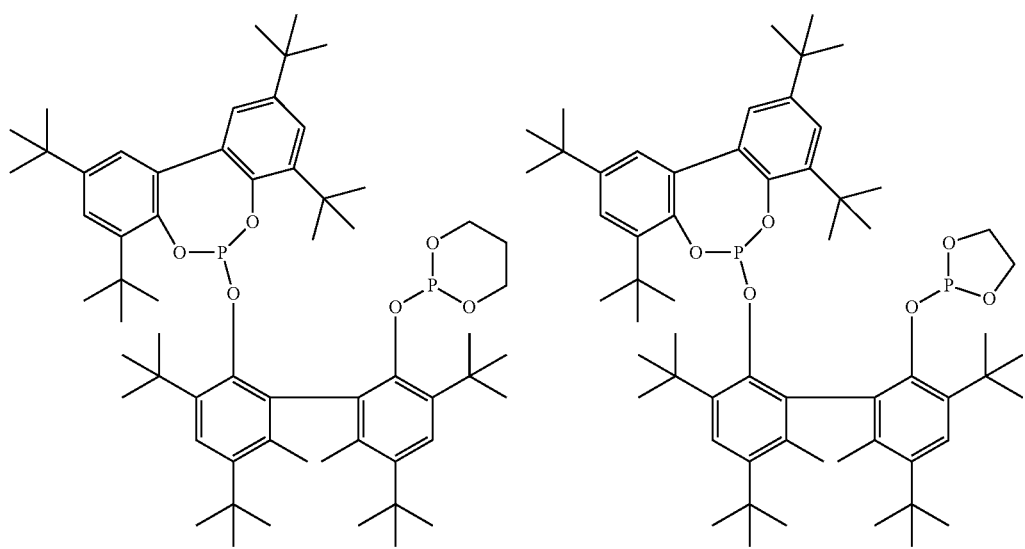

-continued
27
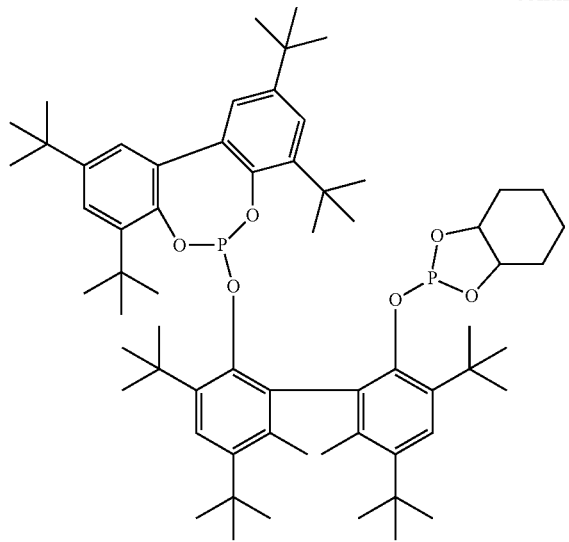
28
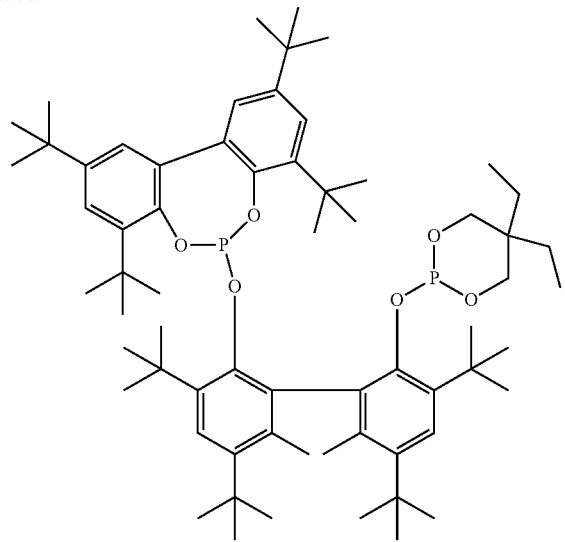
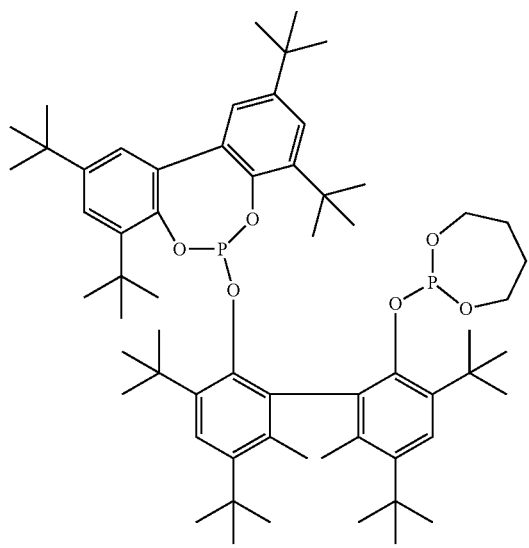
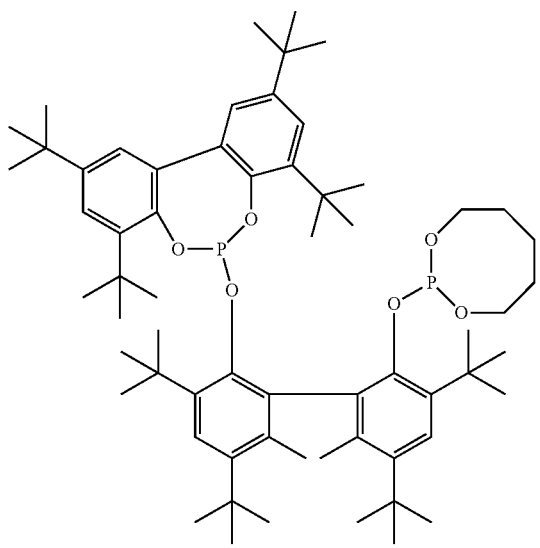
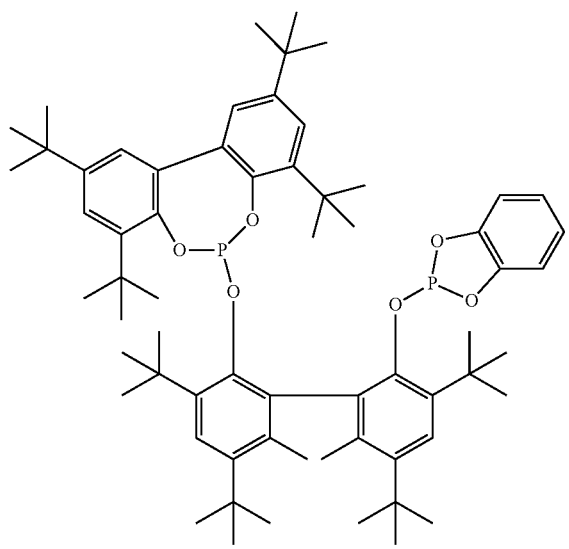

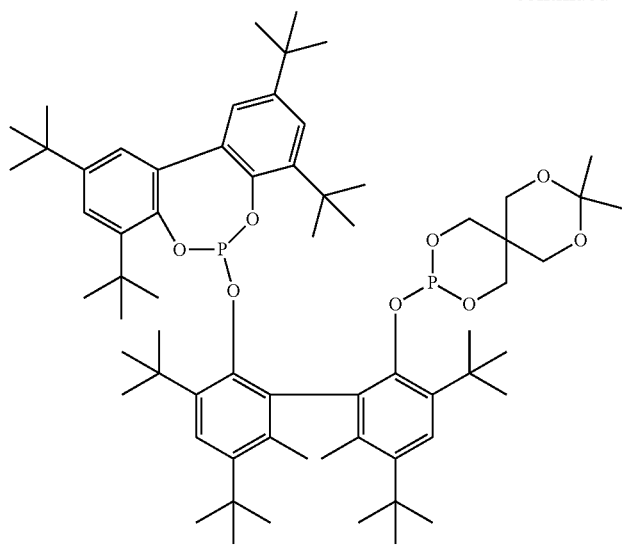
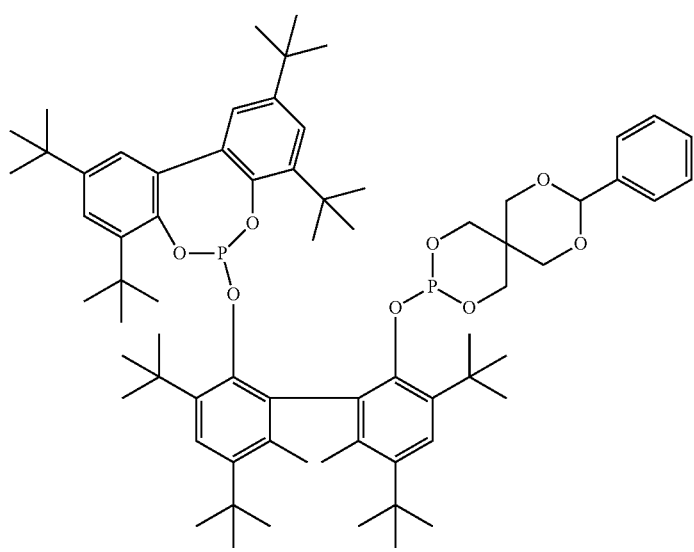
[Chem. 16]
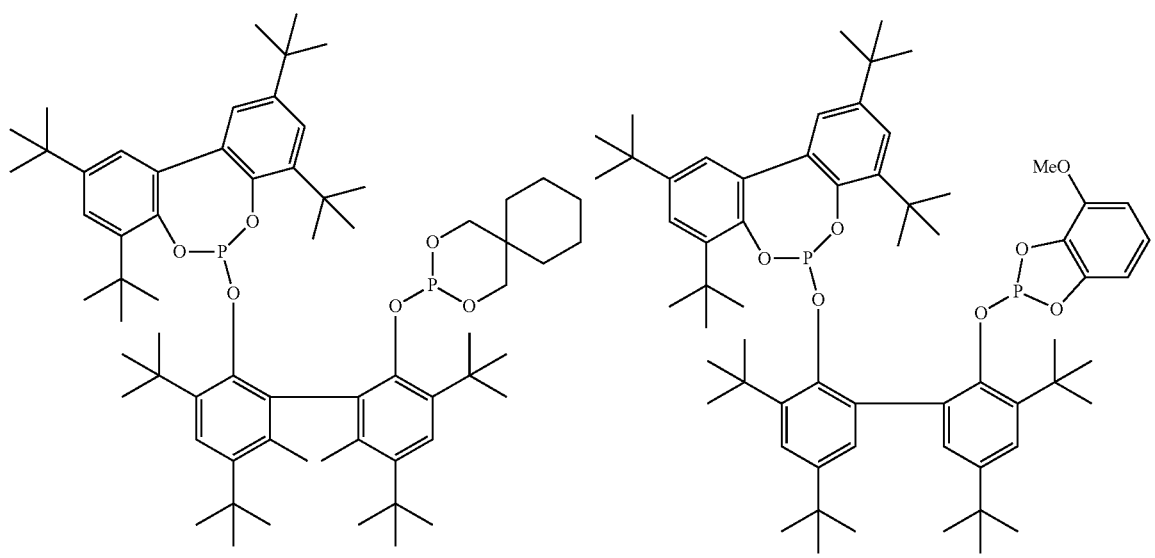

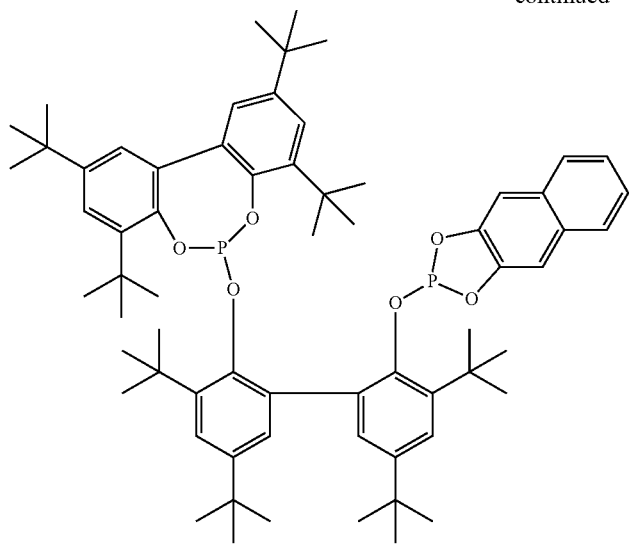
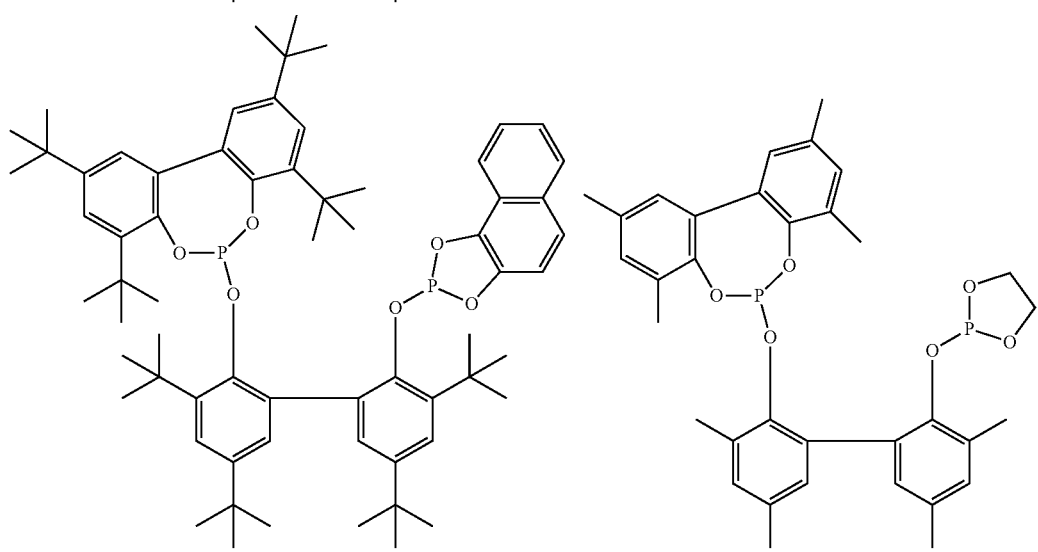
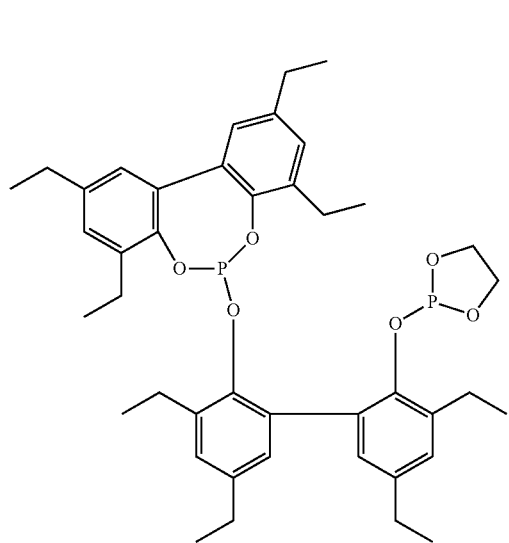
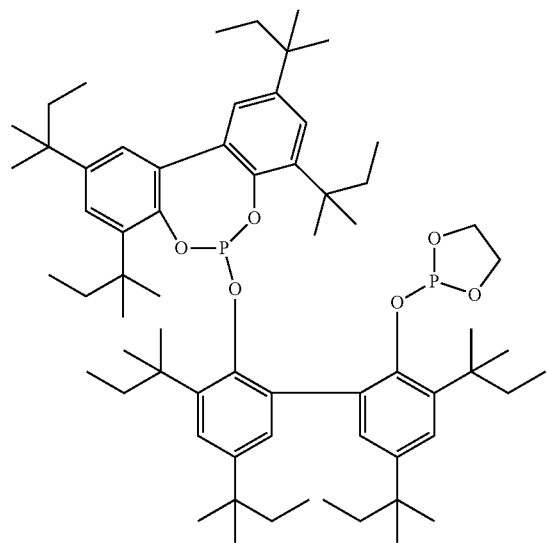

33
34
-continued
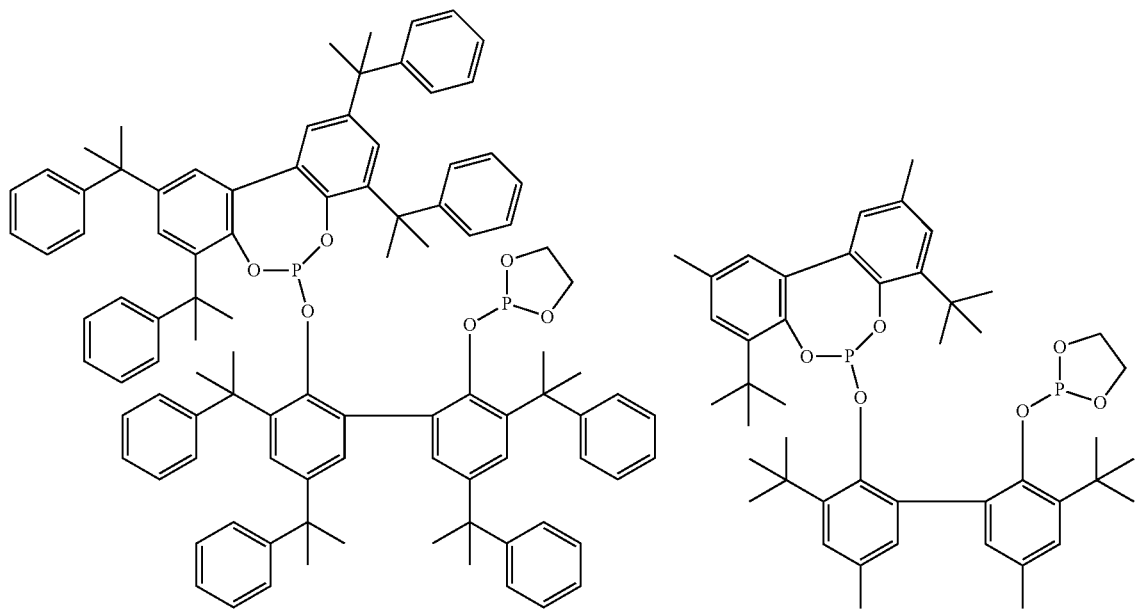
[Chem. 17]
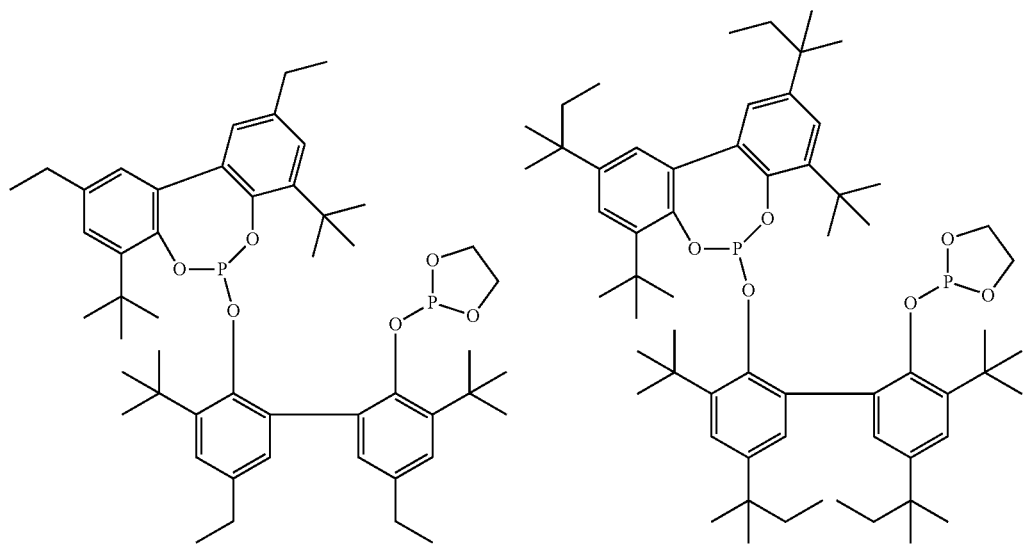

-continued
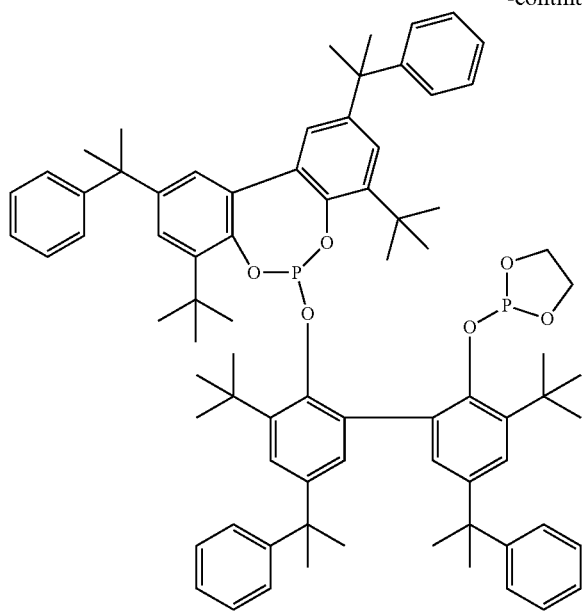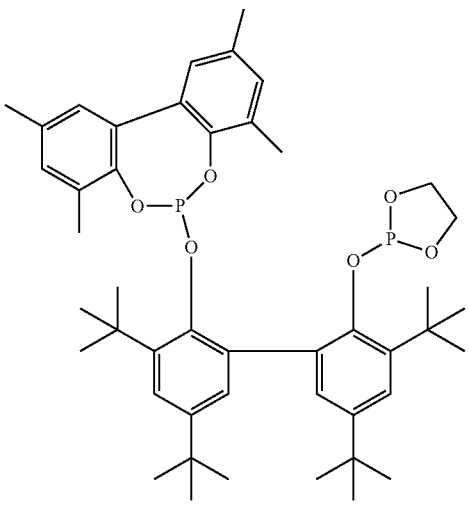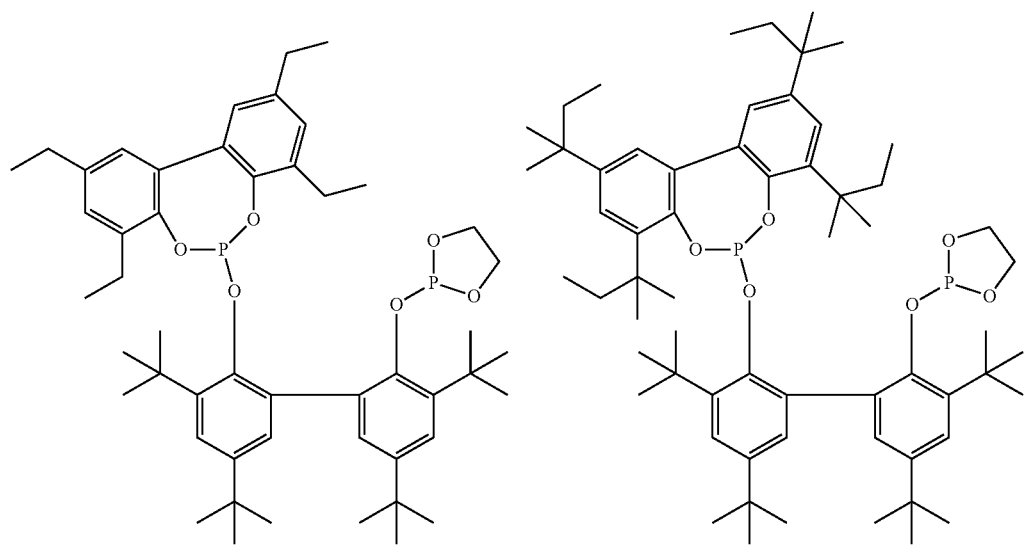

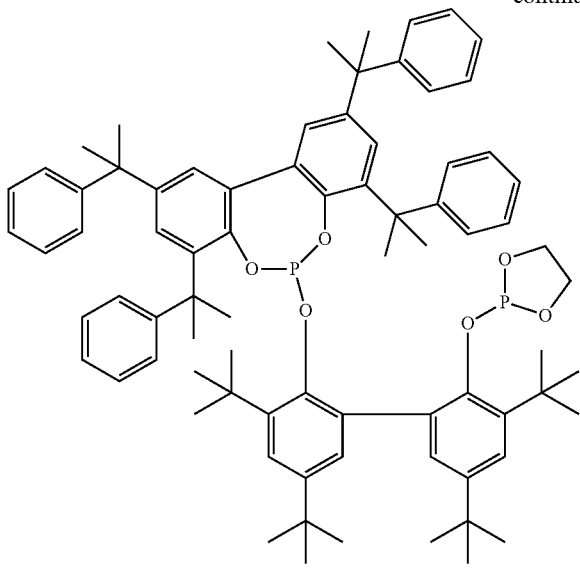

Among the aforementioned ligands, the compounds represented by the formulae (3) and (5) are preferred from the standpoint of the enhancement of the yield of the dialdehyde compound (2). The compound represented by the formula (3) is preferred from the standpoint of the reaction rate, and the compound represented by the formula (5) is preferred from the standpoint of the suppression of the by-product.

The amount of the ligand used is not particularly limited, and the amount of the ligand in terms of coordinating atom per 1 mol of the metal in the Groups 8 to 10 metal compound is preferably in a range of from 1 to 1,000 mol, more preferably in a range of from 2 to 500 mol, and from the standpoint of the reaction rate, further preferably in a range of from 3 to 200 mol. In the case where the amount of the ligand in terms of coordinating atom per 1 mol of the metal in the Groups 8 to 10 metal compound is less than 1 mol, the stability of the catalyst may be impaired, and in the case where the amount thereof exceeds 1,000 mol, there is a tendency that the reaction rate is decreased.

The hydroformylation reaction may be performed in the presence or absence of a solvent. Examples of the solvent include a saturated aliphatic hydrocarbon, such as pentane, hexane, heptane, octane, nonane, decane, and cyclohexane; an aromatic hydrocarbon, such as benzene, toluene, ethylbenzene, propylbenzene, xylene, and ethyltoluene; an alcohol, such as isopropyl alcohol, isobutyl alcohol, isopentyl alcohol, neopentyl alcohol, ethylene glycol, 1,2-propanediol, 1,3-propanediol, 1,2-butanediol, 1,4-butanediol, diethylene glycol, and triethylene glycol; an ether, such as dimethyl ether, ethyl methyl ether, diethyl ether, dipropyl ether, butyl methyl ether, t-butyl methyl ether, dibutyl ether, ethyl phenyl ether, diphenyl ether, tetrahydrofuran, 1,4-dioxane, diethylene glycol dimethyl ether, triethylene glycol dimethyl ether, and tetraethylene glycol dimethyl ether; and a ketone, such as acetone, ethyl methyl ketone, methyl isopropyl ketone, diethyl ketone, ethyl propyl ketone, and dipropyl ketone. The solvents may be used alone or as a combination of two or more kinds thereof. Among these, an aromatic hydrocarbon is preferred, and toluene, ethylbenzene, and xylene are more preferred, from the standpoint of the solubility of the catalyst and the stability thereof under the reaction condition. In the case where the solvent is used, the amount of the solvent used is not particularly limited, and is generally preferably in a range of from 1 to 90% by mass based on the total amount of the reaction mixed liquid.

The reaction temperature in the hydroformylation reaction is preferably in a range of from 40 to 170° C., and from the standpoint of the suppression of the catalyst deactivation, more preferably in a range of from 50 to 150° C. The reaction pressure is preferably in a range of from 0.01 to 15 MPa (gauge pressure), and more preferably in a range of from 0.5 to 10 MPa (gauge pressure), from the standpoint of the reactivity and the stability of the catalyst. The reaction time is generally in a range of from 0.5 to 20 hours, and preferably in a range of from 0.5 to 10 hours.

The implementation method of the hydroformylation reaction is not particularly limited, and for example, the aldehyde compound (1) is charged in the presence of a mixed gas of carbon monoxide and hydrogen (molar ratio: 1/1), and a mixed solution of the ligand, the Groups 8 to 10 metal compound, and the solvent is supplied under agitation, followed by performing the reaction at the prescribed temperature and the prescribed pressure.

The molar ratio of carbon monoxide and hydrogen is preferably in a range of from 0.01 to 50, and from the standpoint of the reactivity and the reaction selectivity, more preferably in a range of from 0.1 to 10.

The reaction may be performed by a batch system or a continuous system, by using an agitating reaction tank, a circulating reaction tank, a bubble column reaction tank, or the like. Depending on necessity, the unreacted aldehyde compound (1) may be recovered from the reaction liquid after completing the reaction, and recycled to the reactor for performing the reaction. The continuous system may be performed with a single reactor or plural reactors connected in series or parallel.

The method for isolating and purifying the dialdehyde compound (2) from the reaction mixed liquid obtained by the aforementioned method is not particularly limited, and the ordinary method used for isolating and purifying an organic compound may be used. For example, after distilling off the solvent, the basic compound, and the like from the reaction mixed liquid, the residue is distilled under reduced pressure, thereby providing the dialdehyde compound (2)

having high purity. Before the distillation, the ligand and the Groups 8 to 10 metal compound may be isolated by subjecting to such a method as evaporation, extraction, and adsorption. The ligand and the Groups 8 to 10 metal compound isolated may be used again for the hydroformylation reaction. The resulting dialdehyde compound (2) may be stored after diluting with a solvent, such as water, for preventing polymerization from occurring.

EXAMPLES

The present invention will be described with reference to examples and the like below, but the present invention is not limited to the examples.

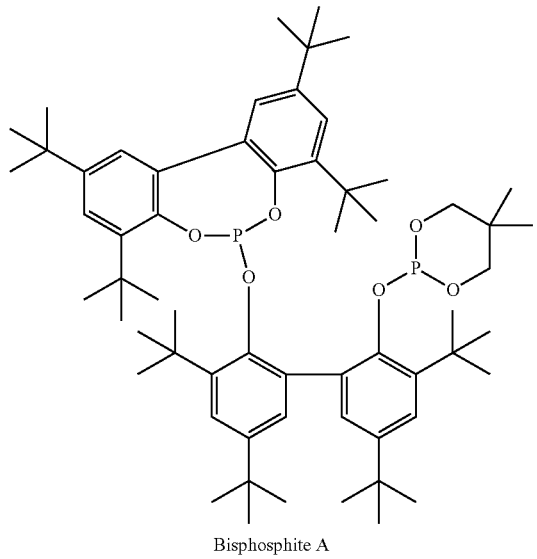 [SMILES: CC1(C)COP(Oc2c(-c3cc(C(C)(C)C)cc(C(C)(C)C)c3Op3oc4c(C(C)(C)C)cc(C(C)(C)C)cc4c4cc(C(C)(C)C)cc(C(C)(C)C)c4o3)cc(C(C)(C)C)cc2C(C)(C)C)OC1]

Bisphosphite A

Example 1

A solution containing 0.98 g of bisphosphite A and 13.2 mg of Rh(acac)(CO)$_2$ dissolved in 50 mL of toluene was prepared (rhodium atom/phosphorus atom=1/20 (molar ratio)). To an electromagnetic agitation autoclave equipped with a gas introduction port and a sampling port, under a nitrogen atmosphere, 28 mL of toluene, 8 mL of 3-methyl-3-buten-1-al, and 4 mL of the catalyst liquid prepared above were added (rhodium compound concentration in reaction system: 0.1 mmol/L), and after making the interior of the autoclave to 8 MPa (gauge pressure) with a mixed gas of carbon monoxide and hydrogen (molar ratio: 1/1), the temperature inside the autoclave was increased to 130° C. under agitation, and the reaction was performed for 6 hours. During the reaction, the mixed gas of carbon monoxide and hydrogen (molar ratio: 1/1) was continuously supplied to retain the pressure inside the reaction system constant. The analysis of the resulting reaction liquid by gas chromatography revealed that the conversion of 3-methyl-3-buten-1-al was 75.9%, and the selectivity of MGL was 66.1%.

Example 2

The reaction was performed in the same manner as in Example 1 except that 3.23 g of tris(2,4-di-t-butylphenyl)phosphite (electronic parameter: 2,085.1 cm$^{-1}$, steric parameter: 175°) was used instead of bisphosphite A (rhodium atom/phosphorus atom=1/100 (molar ratio)), and the reaction time was 3 hours. The conversion of 3-methyl-3-buten-1-al was 79.2%, and the selectivity of MGL was 41.0%.

Example 3

The reaction was performed in the same manner as in Example 1 except that 1.31 g of triphenylphosphine (electronic parameter: 2,069.1 cm$^{-1}$, steric parameter: 145°) was used instead of bisphosphite A (rhodium atom/phosphorus atom=1/100 (molar ratio)), and the reaction time was 4.5 hours. The conversion of 3-methyl-3-buten-1-al was 93.6%, and the selectivity of MGL was 34.1%.

INDUSTRIAL APPLICABILITY

According to the present invention, 1,5-pentanedial having an alkyl group at the 3-position, which is useful as a curing agent for a photosensitive material, a leather tanning agent, and a synthetic intermediate, can be produced under mild conditions with a good yield.

The invention claimed is:

1. A method of producing a dialdehyde compound represented by the following general formula (2):

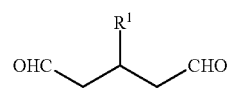

(2)

wherein R$^1$ represents an alkyl group having from 1 to 6 carbon atoms,
the method comprising a step of hydroformylating an aldehyde compound represented by the following general formula (1):

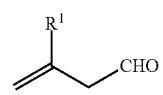

(1)

wherein R$^1$ has the same definition as above.

2. The production method according to claim 1, wherein the hydroformylating step is performed in the presence of a Groups 8 to 10 metal compound and a ligand.

3. The production method according to claim 2, wherein the Groups 8 to 10 metal compound is a rhodium compound.

4. The production method according to claim 2, wherein the ligand is a compound represented by the following general formula (5):

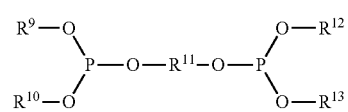

(5)

wherein R$^9$, R$^{10}$, R$^{12}$, and R$^{13}$ each independently represent a hydrocarbon group having from 1 to 40 carbon atoms, which may have a substituent, in which R$^9$ and R$^{10}$, and R$^{12}$ and R$^{13}$ each may be bonded to each other;

and R[11] represents a hydrocarbon crosslinking group having from 1 to 40 carbon atoms, which may have a substituent.

5. The production method according to claim 3, wherein the ligand is a compound represented by the following general formula (5):

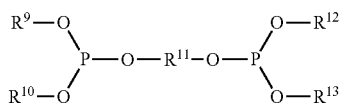
(5)

wherein R[9], R[10], R[12], and R[13] each independently represent a hydrocarbon group having from 1 to 40 carbon atoms, which may have a substituent, in which R[9] and R[10], and R[12] and R[13] each may be bonded to each other; and R[11] represents a hydrocarbon crosslinking group having from 1 to 40 carbon atoms, which may have a substituent.

6. The production method according to claim 1, wherein the hydroformylating is conducted at 40 to 170° C.

7. The production method according to claim 1, wherein the hydroformylating is conducted at 50 to 150° C.

8. The production method according to claim 1, wherein the hydroformylating is conducted at 0.01 to 15 MPa.

9. The production method according to claim 1, wherein the hydroformylating is conducted at 0.5 to 10 MPa.

10. The production method according to claim 7, wherein the hydroformylating is conducted at 0.5 to 10 MPa.

11. The production method according to claim 2, wherein the hydroformylating is conducted at 50 to 150° C.

12. The production method according to claim 2, wherein the hydroformylating is conducted at 0.5 to 10 MPa.

13. The production method according to claim 11, wherein the hydroformylating is conducted at 0.5 to 10 MPa.

* * * * *